Jan. 17, 1939. V. MKHALIAN Plant Pat. 311
GRAPE
Filed March 29, 1938
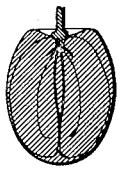
INVENTOR
Vahan Mkhalian
BY
ATTORNEY Patented Jan. 17, 1939

Plant Pat. 311

UNITED STATES PATENT OFFICE

311

GRAPE

Vahan Mkhalian, Visalia, Calif.

Application March 29, 1938, Serial No. 198,663

1 Claim. (Cl. 47—62)

This invention or discovery relates in general to grapes, and is directed in particular to a grape which closely resembles the Emperor variety which is one of the standard shipping grapes grown in the San Joaquin Valley of California. My new grape is of especial commercial value due to the fact that it is entirely seedless.

The grape herein described was discovered by me growing in my vineyard at Visalia, Tulare County, California, on a grape vine of the Emperor type, in the month of November, 1928, and since its discovery I have successfully asexually reproduced the same by grafting and by making cuttings from the newly discovered wood. The vines of the new variety which I have grown in my vineyard are trained on a trellis as a bilateral cordon which is the generally accepted method of training Emperor grape vines in the growing area. The grapes which have been borne by the vines of the new variety have fully retained the seedless characteristic although they otherwise closely resemble the Emperor grape of the parent vine. I regard my new variety as a seedless sport of the Emperor grape.

The figure of the original drawing is a median section of one of the berries of the new variety of grape.

The following description sets forth the characteristics of the new variety of grape which I have discovered.

*Vine.*—The vine of the new variety of grape is vigorous and, when so trained, quite upright as well as being dense, hardy, and productive. The trunk of the vine is of medium size, the bark is loose and shreddy, and the canes are of medium size, long, numerous, straight and brown. The nodes are enlarged while the internodes are short. The tendrils are intermittent but frequent, of medium size, bifurcated and smooth.

*Flowers.*—The flowers are fertile, mid-season (bloom in the latter part of May in an ordinary season), and the stamens are upright.

*Leaves.*—The leaves are large, cordate, and of medium thickness while the upper surface thereof is medium, dull, and dark green which turns medium bronze at maturity. The lower surface of the leaves is pale green and downy. There are five lobes and the terminal lobe is acuminate. The petiolar sinus is of medium width and depth and is overlapping; the basal sinus being shallow and narrow and the lateral sinus is deep and narrow. The margin is dentate, and the teeth shallow and wide.

*Fruit.*—The clusters of fruit are of medium size both in length and width, as well as being tapering, regular and double-shouldered. As to compactness, the clusters are medium. The peduncle is medium and slender while the pedicel is long, medium and with warts. The brush is short and yellow. The berry is strongly adherent, medium and uniform as well as oval with a tendency toward obovoid (elongated). In color the berries are light purple and red with a medium bloom. The skin is medium and separates from the pulp. The flesh of the berries is greenish, transparent and meaty as well as tender, juicy, clear and sweet and subsequent to subacid. The quality of the berries is very good.

*Seeds.*—The grapes are entirely seedless and this is their novel characteristic and the one which distinguishes the new variety from the Emperor variety.

*Ripening period.*—The above described new variety of grape ripens and is harvested in the San Joaquin Valley of California during the months of October, November and December. A large portion of the annual crop of Emperor variety of grape is picked and placed in storage at harvest for the holiday season which closely follows the harvest period, and the grapes of the new variety appear to be as well suited to storage as the Emperor variety. Grapes of the new variety have been placed in storage for a period of over two months and thereafter were found to be quite usable.

*Use.*—The new variety of grape is particularly suited for use as a shipping and market grape and for home consumption and the like.

As will be obvious, the new variety of grape described above closely resembles the Emperor variety in every substantial respect except that such new variety is totally lacking in seeds. The new variety is harvested at substantially the same time and will produce substantially the same average crop of grapes as the Emperor variety and, in addition to such qualities, has the very important advantage of being a seedless grape.

The above described characteristics are of course typical and may be subject to certain variations as all varieties of grapes differ to a certain extent among themselves in adaption to any particular region, soil or climatic conditions.

Having thus described my invention or discovery, what I claim as new and useful and desire to secure by Letters Patent is:

The herein described grape of the Emperor type characterized by its seedlessness.

VAHAN MKHALIAN.